US010151745B2

United States Patent
Hermine et al.

(10) Patent No.: US 10,151,745 B2
(45) Date of Patent: Dec. 11, 2018

(54) METHODS FOR DETERMINING THE RISK OF ACUTE GRAFT VERSUS HOST DISEASE

(71) Applicants: INSERM (Institut National De La Santé Et De La Recherche Médicale), Paris (FR); Centre National de la Recherche Scientifique (CNRS), Paris (FR); Assistance Publique—Hopitaux de Paris, Paris (FR); Université Paris Descartes, Paris (FR); Imagine Institut des Maladies Genetiques Necker Enfants Malades, Paris (FR)

(72) Inventors: Olivier Hermine, Paris (FR); Marie Thérèse Rubio, Paris (FR); Marie Bouillie, Paris (FR); Maria Leite de Maraes, Paris (FR)

(73) Assignees: Institut National de la Sante et de la Recherche Medicale (INSERM), Paris (FR); Centre National de la Recherche Scientifique (CNRS), Paris (FR); Assistance Publique—Hopitaux de Paris, Paris (FR); Universite Paris Descartes, Paris (FR); Imagine Institut des Maladies Genetiques Necker Enfants Malades, Paris (FR)

( * ) Notice: Subject to any disclaimer, the term of this patent is extended or adjusted under 35 U.S.C. 154(b) by 44 days.

(21) Appl. No.: 14/646,486

(22) PCT Filed: Nov. 21, 2013

(86) PCT No.: PCT/EP2013/074407
§ 371 (c)(1),
(2) Date: May 21, 2015

(87) PCT Pub. No.: WO2014/079946
PCT Pub. Date: May 30, 2014

(65) Prior Publication Data
US 2015/0301022 A1     Oct. 22, 2015

(30) Foreign Application Priority Data
Nov. 21, 2012 (EP) .................................. 12306445

(51) Int. Cl.
*G01N 33/50* (2006.01)
*G01N 33/569* (2006.01)
*G01N 33/68* (2006.01)

(52) U.S. Cl.
CPC ..... *G01N 33/505* (2013.01); *G01N 33/56972* (2013.01); *G01N 33/6893* (2013.01); *G01N 2333/55* (2013.01); *G01N 2333/7051* (2013.01); *G01N 2333/70514* (2013.01); *G01N 2800/245* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

| WO | WO 93/05055 | 3/1993 |
|----|-------------|--------|
| WO | WO 94/02168 | 2/1994 |
| WO | WO 94/09020 | 4/1994 |
| WO | WO 94/24142 | 10/1994 |
| WO | WO 98/44928 | 10/1998 |
| WO | WO 2009/062160 | 5/2009 |

OTHER PUBLICATIONS

Chaidos et al. (Blood, 119(21): 5030-5036, May 2012).*
Chaidos et al. (Blood, 116: 2539, 2010, Abstract 2539).*
Exley et al. (Eur. J. Immunology, 38: 1756-1766, 2008).*
Bendelac et al., *The Biology of NKT Cells*, 25 Annu. Re. Immunol. 297-336 (2007).
Chaidos et al., *Graft invariant natural killer T-cell dose predicts risk of acute graft-versus-host disease in allogeneic hematopoietic stem cell transplantation*, 119(21) Blood 5630-5036 (Sep. 6, 2012).
Rubio et al., *Early posttransplantation donor-derived invariant natural killer T-cell recovery predicts the occurrence of acute graft-versus-host disease and overall survival*, 120(10) Blood 2144-2154 (Sep. 6, 2012).

* cited by examiner

*Primary Examiner* — Nelson B Moseley, II
(74) *Attorney, Agent, or Firm* — Buchanan Ingersoll & Rooney PC

(57) ABSTRACT

The present invention relates to a method for determining whether a candidate human transplant donor is at risk of inducing acute graft versus host disease (aGVHD) in a human transplant recipient, which may in turn allow the selection of a donor exhibiting no risk for the recipient. The present invention also relates to a method for adjusting the immunosuppressive treatment administered to a human transplanted recipient following its graft transplantation after having performing the method for determining risk of the invention. The methods comprise expanding the candidate donor's iNKT cells (invariant NKT cells) and determining the presence or absence of expansion of the CD4(−) iNKT cell sub-population. In particular, CD3+CD4− TCRV[alpha]24V[beta]11 cells are determined. Kits are disclosed.

12 Claims, 4 Drawing Sheets

METHODS FOR DETERMINING THE RISK OF ACUTE GRAFT VERSUS HOST DISEASE

CROSS-REFERENCE TO RELATED APPLICATIONS

Figure 1:
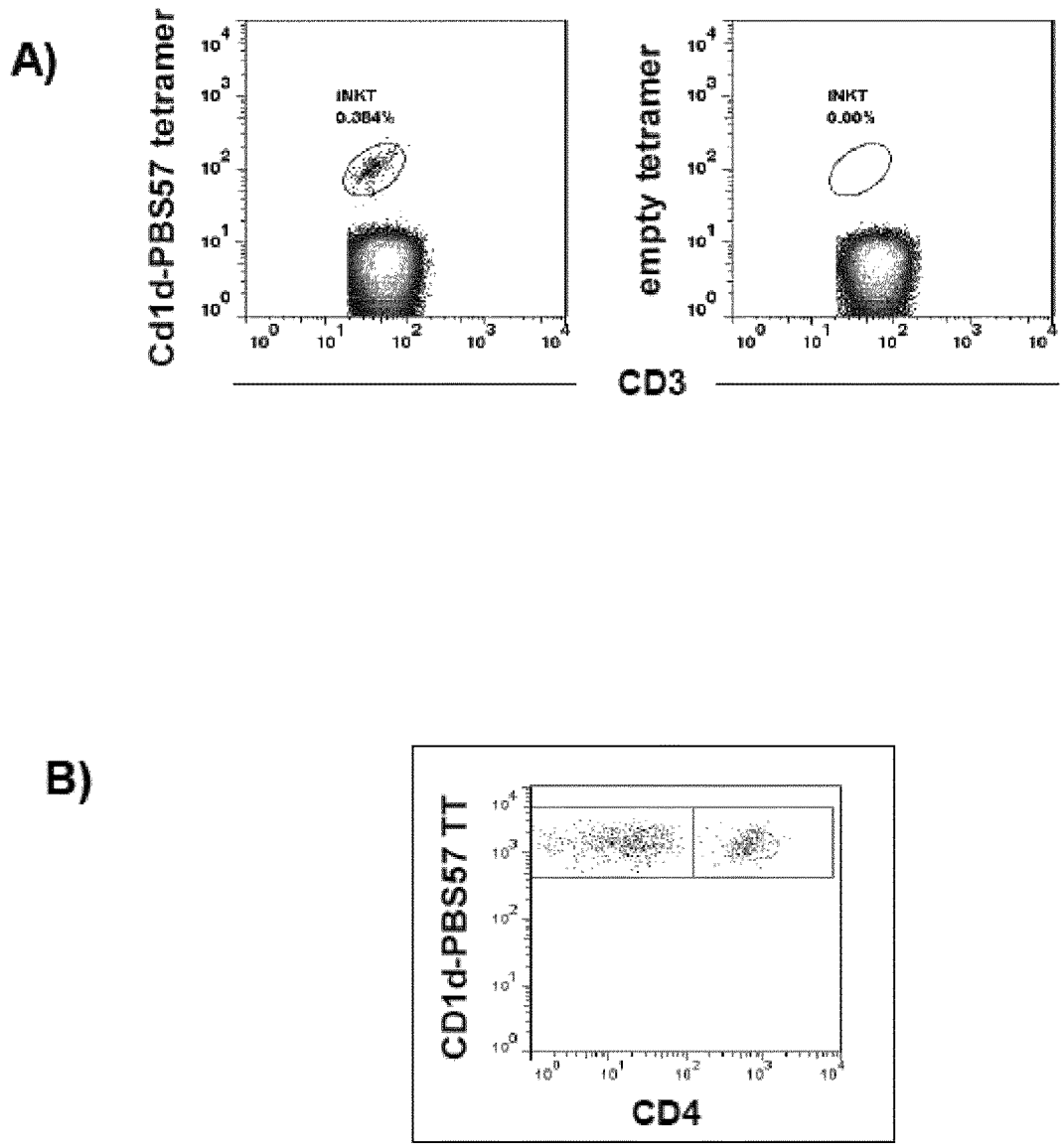

This application is a U.S. National Stage Application pursuant to 35 U.S.C. § 371 of International Patent Application PCT/EP2013/074407, filed on Nov. 21, 2013, and published as WO 2014/079946 on May 30, 2014, which claims priority to European Patent Application 12306445.3, filed on Nov. 21, 2012, all of which are incorporated herein by reference in their entireties for all purposes.

FIELD OF THE INVENTION

The invention relates to methods and corresponding products (e.g. kits) for the prediction of risk of acute graft versus host disease as well as corresponding methods for selecting a transplant donor and for adjusting treatment associated with such risk prediction.

BACKGROUND OF THE INVENTION

First lines of therapy for hematological malignancies generally include chemotherapy and/or chemo-immunotherapy with monoclonal antibodies. However, some patients experience relapse or progression of the disease and become sometimes refractory to standard treatment.

Immune therapy including allogenic stem cell transplantation (SCT) represents an alternative way for therapy in these patients who are difficult to cure or less likely to be cured with standard chemotherapy. Hematopoietic stem cell transplantation (HSCT) is a therapy that involves taking hematopoietic stem cells from a donor or from cord blood and infusing them intravenously to the recipient conditioned to accept the transplant. However, the overall survival rate after transplantation is still only of 40% to 60% due to severe posttransplant complications including graft versus host disease (GVHD). GVHD is a generic name for diseases that are caused by the immune reaction of transferred or transplanted immunocompetent cells (e.g., mature T cells) against host tissues and that can induce severe organ toxicity leading to death in some cases.

Therefore, human leukocyte antigen (HLA) matching is essential to reduce the risk of graft rejection and GVHD. However, non-HLA genes also impact on transplant outcome and GVHD can be fatal even in patients receiving transplants from HLA-identical matched sibling donors (MSD). Furthermore, MSD are only available for about one third of the patients and, therefore, alternative donors are needed. HLA-matched unrelated donors (MUD) are more widely used than cord blood or mismatched related donors but the risk of GVHD must also be taken in consideration for patients receiving transplants from MUD.

Accordingly, there is still a need for methods useful for predicting the risk of developing GVHD in patients receiving transplants (or conversely methods for determining whether a candidate donor is at risk of inducing GVHD in a recipient).

Recently, two retrospective studies have demonstrated the clinical relevance of invariant NKT (iNKT) cells in the prediction of acute graft versus host disease (aGVHD) by analyzing the frequency distribution of effector and regulatory lymphocytes in peripheral blood stem cell (PBSC) of recipients of allogeneic HSCT (Rubio et al., Blood 2012) or of donor grafts (Chaidos et al., 2012). An impaired reconstitution of iNKT cells in the recipients or a low CD4− iNKT cell dose in the graft were shown to represent independent parameters that can significantly predict the occurrence of aGVHD after HSCT.

However, a method predicting the risk of developing aGVHD based on the direct determination in blood or graft samples of iNKT cells is not satisfying for physicians since the threshold between low and high iNKT cells is difficult to determine leading for instance to a risk of error for intermediate results.

SUMMARY OF THE INVENTION

In a first aspect, the invention relates to a method for determining whether a candidate human transplant donor is at risk of inducing acute graft versus host disease (aGVHD) in a human transplant recipient, comprising the following steps of: i) expanding the population of invariant NKT (iNKT) cells from a biological sample obtained from the candidate human transplant donor; ii) detecting the presence or absence of expansion of the CD4− iNKT cell subpopulation in the population obtained at step i); and iii) concluding that the candidate human transplant donor has an increased risk of inducing aGVHD in a human transplant recipient when the subpopulation CD4− iNKT cells does not expand from the population of iNKT cells.

In a second aspect, the invention relates to a method for selecting a human transplant donor in order to reduce the risk of inducing aGVHD in a human transplant recipient, comprising the following steps of (i) performing the method for determining risk according to the invention, and (ii) selecting said donor in accordance with said risk determination.

In a third aspect, the invention relates to a method for adjusting the immunosuppressive treatment administered to a human transplanted recipient following its graft transplantation, comprising the following steps of (i) performing the method for determining risk according to the invention, and (ii) adjusting the immunosuppressive treatment.

In another aspect the invention further relates to a kit for performing the methods according to the invention above described.

DETAILED DESCRIPTION OF THE INVENTION

The inventors have shown that a previous step of expanding during 12 or 15 days the population of iNKT cells from a PBSC graft or a blood sample obtained from a candidate donor before analyzing the expansion capacity of the CD4− iNKT cell subpopulation allows to safely determining whether said a candidate donor is at risk of inducing acute GVHD in a recipient. Indeed, after said expansion, there are only two distinct possibilities: either the subpopulation of CD4− iNKT cells has not expanded (expansion factor≤1) from the population of iNKT cells and therefore the donor has an increased risk of inducing acute GVHD in the recipient, or the subpopulation CD4− iNKT cells has significantly expanded (expansion factor>1) from the population of iNKT cells and therefore the donor has almost no risk of inducing acute GVHD in the recipient.

A Method for Determining the Risk of Acute Graft Versus Host Disease (aGVHD)

Accordingly, in a first aspect, the present invention relates to a method for determining whether a candidate human transplant donor is at risk of inducing acute graft versus host disease (aGVHD) in a human transplant recipient, comprising the following steps of: i) expanding the population of invariant NKT (iNKT) cells from a biological sample obtained from the candidate human transplant donor; ii) detecting the presence or absence of expansion of the subpopulation CD4− iNKT cells in the population obtained at step i); and iii) concluding that the candidate human transplant donor has an increased risk of inducing aGVHD in a human transplant recipient when the CD4− iNKT cell subpopulation does not expand from the population of iNKT cells.

As used herein, the term "risk" refers to the probability that an event will occur over a specific time period, such as the onset of acute GVHD (aGVHD), and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk determination" in the context of the present invention encompasses making a prediction of the probability, odds, or likelihood that an event may occur. Risk determination can also comprise prediction of future clinical parameters, traditional laboratory risk factor values, or other indices of aGVHD, such age, sex mismatch, HLA-testing, etc . . . ; either in absolute or relative terms in reference to a previously measured population. The methods of the present invention may be used to make categorical measurements of the risk of inducing aGVHD in a transplant recipient, thus defining the risk spectrum of a category of transplant donors defined as being at risk of inducing aGVHD or not and thus is useful for selecting a safe donor.

As used herein, the term "transplant donor" refers to a subject to whom an organ, tissue or cell to be transplanted is harvested from. As used herein, the term "transplant recipient" refers to a subject who will receive a transplanted organ, tissue or cell. As used herein, the term "transplant" (or "graft") refers to the free (unattached) cells, tissue, or organ integrates into a tissue following transplantation into a subject. Within the context of hematopoietic stem cell transplantation (HSCT), the transplant is multipotent hematopoietic stem cells, usually derived from peripheral blood after mobilization by G-CSF, bone marrow or umbilical cord blood.

As used herein, the term "biological sample" refers to any sample isolated from a subject (e.g. a transplant donor), preferably a sample which contain peripheral blood mononuclear cells (PBMCs). Examples of such samples include fluids, tissues, cell samples, organs, biopsies, etc. Most preferred samples are blood sample, cord blood sample or graft sample (e.g. Peripheral Blood Stem Cell (PBSC) graft sample or Bone Marrow (BM) graft sample).

As used herein, the term "blood sample" refers to a sample which includes whole blood, plasma and serum.

As used herein, the term "NKT cells" (Natural Killer T cells) refers to a subpopulation of lymphocytes and more particularly to a unique subset of CD1d-restricted T cells that provide a link between innate and adaptive immune responses. Indeed, NKT cells, co-expressing a T cell receptor and NK cell markers, are essential for several aspects of immunity in various immune diseases including autoimmune diseases, infectious diseases and cancer. Unlike conventional T cells that recognize small peptide antigens presented by major histocompatibility complex (MHC) MHC class 1 or MHC class 2, NKT cells recognize glycolipid antigens presented by CD1d, a MHC class 1-like molecule.

As used herein, the term "iNKT" (invariant NKT cells) refers to a major subset of NKT cells, also called type 1 NKT cells expressing an invariant natural T cell receptor (TCR) composed of V[alpha]14-J[alpha]18 chains in mice (V[alpha]24-J[alpha]18 in humans). Upon TCR stimulation with a ligand, such as alpha-galactosylceramide, iNKT cells rapidly produce a wide range of cytokines including IL-4, IFN-[gamma], IL-12, and GM-CSF. It should be further noted that iNKT cells comprise two main subsets (or subpopulations), namely CD4+ and CD4− cells, which in humans have distinct cytokine secretion profiles. This rapid and potent response to a ligand enables iNKT cells to enhance or regulate the activity of various immune cells in innate and acquired immunity.

In one embodiment, the aGVHD is a grade II-IV aGVHD.

In one embodiment, the candidate human transplant donor is an HLA-identical matched sibling donor (MSD). In another embodiment, the candidate human transplant donor is an HLA-matched unrelated donor (MUD). In still another embodiment, the candidate human transplant donor is a mismatch unrelated donor. Transplant can also be from a haploidentical donor or from a 4/6 to 6/6 HLA (A, B, DR) compatible cord blood.

In one embodiment, the subpopulation of CD4− iNKT cells is a population of CD3+CD4− TCR Vα24Vβ11 cells.

The step (i) of expanding the population of iNKT cells may be carried out by different methods using either non-specific or antigen-specific stimulation known by the skilled man in the art. Typically, said expansion may be obtained by culturing the population of iNKT cells with a glycolipid antigen (e.g. alpha-galactosylceramide (alpha-GalCer)).

As used herein, the term "expanding" refers to the process of activating and amplifying a given population of cells (e.g. immune cells such as T cells). Expansion of T cells is preferably performed by culturing a cell population comprising T cells in the presence of T cell and/or antigen-specific stimulating agent or such as antigens, cells, antibodies, lectins, etc. Expansion may also require culture of T cells in the presence of a cytokine.

The step (ii) of detecting the presence or absence of expansion of the CD4− iNKT cell subpopulation may be carried out by a variety of methods for detecting a particular immune cell population available for a skilled artisan, including immunoselection techniques, such as high-throughput cell sorting using flow cytometric methods, affinity methods with antibodies labeled to magnetic beads, biodegradable beads, non-biodegradable beads, and combination of such methods.

As used herein, the term "flow cytometric methods" refers to a technique for counting cells of interest, by suspending them in a stream of fluid and passing them through an electronic detection apparatus. Flow cytometric methods allow simultaneous multiparametric analysis of the physical and/or chemical parameters of up to thousands of particles per second, such as fluorescent parameters. Modern flow cytometric instruments usually have multiple lasers and fluorescence detectors. A common variation of flow cytometric techniques is to physically sort particles based on their properties, so as to purify or detect populations of interest, using "fluorescence-activated cell sorting". As used herein, "fluorescence-activated cell sorting" (FACS) refers to a flow cytometric method for sorting a heterogeneous mixture of cells from a biological sample into two or more containers, one cell at a time, based upon the specific light scattering and fluorescent characteristics of each cell and provides fast, objective and quantitative recording of fluorescent signals from individual cells as well as physical separation of cells of particular interest. Accordingly, FACS can be used with the methods described herein to isolate and detect the subpopulation of CD4− iNKT cells.

Alternatively, isolation and detection for immune cell populations (e.g. iNKT cells) can be performed using bead based sorting methods, such as magnetic beads.

Using such methods, cells can be separated and detected positively or negatively with respect to the particular cell-surface markers.

As defined herein, "positive selection" refers to techniques that result in the isolation and detection of cells expressing specific cell-surface markers, while "negative selection" refers techniques that result in the isolation and detection of cells not expressing specific cell-surface markers. In some embodiments, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select and detect a subset of iNKT cells (i.e. CD4− iNKT cells).

In such methods, immune cell populations can be isolated and detected with antibodies or other agents, such as tetramers, specifically binding cell-surface marker or antigen.

As used herein, an "agent specifically binding a cell-surface marker" refers to an agent that can specifically react with or bind to that cell-surface marker, but has little or no detectable reactivity to another cell-surface or intracellular marker or antigen. For example, an agent specifically binding CD4 will not bind CD8. Thus, agents specifically binding cell-surface markers recognize unique structural features of said markers. In some embodiments, an agent specifically binding a cell-surface marker binds to the cell-surface marker, but does not cause initiation of downstream signaling events mediated by that cell-surface marker, for example, a non-activating antibody. Agents specifically binding cell-surface marker include, but are not limited to, antibodies or antigen-binding fragments thereof, natural or recombinant ligands, small molecules, nucleic acid sequence and nucleic acid analogues, aptamers and other proteins or peptides.

In some embodiments, the preferred agents are antibodies that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings (Roitt, I. (1991) Essential Immunology, 7th Ed., (Blackwell Scientific Publications, Oxford)]. Such antibodies or antigen-binding fragments are available commercially from vendors such as R&D Systems, BD Biosciences, e-Biosciences, Proimmune and Miltenyi, or can be raised against these cell-surface markers by methods known to those skilled in the art.

In some embodiments, an agent that specifically bind to a cell-surface marker, such as an antibody or antigen-binding fragment, is labelled with a tag to facilitate the isolation and detection of immune cell or iNKT cell populations.

As used herein, the terms "label" or "tag" refer to a composition capable of producing a detectable signal indicative of the presence of a target, such as, the presence of a specific cell-surface marker in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods to isolate and detect immune cells or iNKT cell populations. Non-limiting examples of fluorescent labels or tags for labeling the agents such as antibodies for use in the methods of invention include Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

In one particular embodiment, the population of CD3+ CD4− TCR Vα24Vβ11 cells may be detected by using labelled agent specifically binding CD4 (e.g. a labelled antibody specifically binding CD4), a labelled agent specifically binding CD3 (e.g. a labelled antibody specifically binding CD3) and a labelled agent specifically binding CD1d-restricted TCR Vα24Vβ11 of iNKT cells (e.g. a glycolipid pre-loaded human CD1d-tetramer such as a CD1d/PBS-57 tetramer or those purchased from ProImmune).

In one embodiment, the step i) of expanding the population of iNKT cells is carried out by (a) isolating peripheral blood mononuclear cells (PBMCs) from the biological sample obtained from said candidate human transplant donor, and (b) culturing said PBMCs in a medium comprising both an agent stimulating the proliferation of iNKT cells and an agent activating iNKT cells.

The step (a) of isolating peripheral blood mononuclear cells (PBMCs) from the biological sample obtained from said candidate human transplant donor may carry out by methods well known by the skilled man in the art (e.g. by density centrifugation such Ficoll-Paque™ density-gradient centrifugation).

The step (b) of culturing PBMCs in a medium comprising both an agent stimulating the proliferation of iNKT cells and an agent activating iNKT cells shall be carried out for the necessary time required for the expansion of iNKT cells.

Typically, the culture of PBMCs with a medium of interest shall be carried out for at least 10 days, preferably at least 12 days, even more preferably at least 15 days.

As used herein, the term "medium" refers to a medium for maintaining a cell population, or culturing a cell population (e.g. "culture medium") containing nutrients that maintain cell viability and support proliferation. The medium may contain any of the following in an appropriate combination: salt(s), buffer(s), amino acids, glucose or other sugar(s), antibiotics, serum or serum replacement, and other components such as growth factors, cytokines etc. Media ordinarily used for particular cell types are known to those skilled in the art. The medium of the invention may be based on a commercially available medium such as RPMI1640 from Invitrogen.

As used herein, the term "agent stimulating the proliferation of iNKT cells" refers to any compound, natural or synthetic, which can increase the growing of the iNKT cells.

Advantageously, the agent stimulating the proliferation of iNKT cells is selected from the group consisting of IL-2, IL-7 and IL-15.

In one particular embodiment, the agent stimulating the proliferation of iNKT cells is IL-2. Preferably, IL-2 is a recombinant human interleukin-2 (rhIL-2). It should be further that rhIL-2 is commercially available for pharmaceutical uses. Suitable commercial forms include, e.g. Proleukin®, a recombinant human IL-2 composition.

As used herein, the term "agent activating iNKT cells" refers to any compound, natural or synthetic, which can bind CD1d and activate the invariant natural T cell receptor (TCR) leading to a strong production of Th1 cytokines (e.g. IFN-γ) and/or Th2 cytokines (e.g. IL-4) which in turn amplify or regulate innate/adaptive immune responses by inducing the maturation of dendritic cells (DC) and by influencing the functions of other immune cells such as NK cells, macrophages, and conventional T lymphocytes.

Advantageously, the agent activating iNKT cells is a glycolipid antigen, in particular a glycosphingolipid antigen such alpha-galactosylceramide (alpha-GalCer) and analogues.

As used herein, the term "alpha-galactosylceramide" (alpha-GalCer or (2S,3S,4R)-1-O-(alpha-D-galactosyl)-N-hexacosanoyl-2-amino-1,3,4-octadecanetriol) also named as KRN7000), refers to a marine-sponge derived glycosphingolipid, which is a super-agonist antigen for iNKT cells (described in U.S. Pat. No. 5,936,076).

As used herein, the term "alpha-GalCer analogues" refers to any compound, natural or synthetic, which leads to the same production of cytokines in the way than alpha-GalCer. Thus, such compounds include alpha-GalCer derivatives as well as compounds whose structure is similar to alpha-GalCer and are well known of the skilled man in the art. Other analogues have for instance been described in international patent applications N° WO 93/05055; WO 94/09020; WO 94/24142; WO 94/02168 and WO 98/44928.

In one embodiment, the agent activating iNKT cells is a glycolipid antigen selected from the group consisting of alpha-galactosylceramide (alpha-GalCer), alpha-glucuronosylceramide, phosphatidylinositoltetramannoside, isoglobotrihexosylceramide, ganglioside GD3, phosphatidylcholine, phosphatidylethanolamine, phosphatidylinositol, sulfatide, beta-galactosylceramide, lipophosphoglycan, glycoinositol phospholipid, alpha-galactosylceramide analogs including beta-anomeric galactoceramide and alpha-anomeric galactosylceramide, and bacterial lipid antigens.

In one particular embodiment, the agent activating iNKT cells is alpha-GalCer.

Typically, alpha-GalCer is added to the culture medium of the invention at a concentration ranging from 1 to 500 ng/ml, preferably at 100 ng/ml.

Typically, IL-2 is added to the culture medium of the invention at a concentration ranging from 1 to 100 ng/ml, preferably at 50 ng/ml.

In a preferred embodiment, alpha-GalCer is added to the culture medium of the invention at day 0 and IL-2 is then added to the culture medium at day 1.

Methods for Selecting a Human Transplant Donor

The invention further provides methods for selecting transplant donor. Information gained by way of the methods described above can be used to select a transplant donor among several previously identified compatible donors in order to avoid or minimize the development of acute GVHD.

Thus, in a second aspect, the present invention relates to a method for selecting a human transplant donor in order to reduce the risk of inducing acute GVHD in a human transplant recipient, comprising the following steps of (i) performing the method for determining risk according to claim 1, and (ii) selecting said donor in accordance with said risk determination.

The methods can be carried out by, for example, using any of the methods for determining risk described above and, in consideration of the results obtained, selecting the best transplant donor for the transplant recipient in order to reduce the risk of acute GVHD. If the level of expansion of the CD4− iNKT cell subpopulation indicates that the donor is at risk for of inducing GVHD, it may be necessary to identify another compatible donor Indeed, to limit the risks of transplanted stem cell rejection or of acute GVHD in allogeneic HSCT, the donor should preferably have the same human leukocyte antigens (HLA) as the recipient. A compatible donor is found by doing additional HLA-testing from the blood of potential donors. The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease. Matching is performed on the basis of variability at three or more loci of the HLA gene, and a perfect match at these loci is preferred. Even if there is a good match at these critical alleles, the recipient will require immunosuppressive medications to mitigate graft-versus-host disease. Allogeneic transplant donors may be related (usually a closely HLA matched sibling or MSD) or unrelated (donor who is not related and found to have very close degree of HLA matching or MUD). Unrelated donors may be found through a registry of bone marrow donors such as the International Marrow Donor Program.

Methods for Adjusting an Immunosuppressive Treatment

The invention further provides methods for developing personalized treatment plans. Information gained by way of the methods described above can be used to develop a personalized treatment plan for a transplant recipient.

Accordingly, in a further aspect, the present invention relates to a method for adjusting the immunosuppressive treatment administered to a human transplanted recipient following its graft transplantation, comprising the following steps of (i) performing the methods for determining risk according the invention, and (ii) adjusting the immunosuppressive treatment.

The methods can be carried out by, for example, using any of the methods for determining risk described above and, in consideration of the results obtained, designing a treatment plan for the transplant recipient. If the level of expansion of the CD4− iNKT cell subpopulation indicates that the recipient is at risk for an undesirable clinical outcome (e.g., development of aGVHD), the recipient is a candidate for treatment with an effective amount of an immunosuppressive treatment (e.g. by an anti-rejection agent). Depending on the level of expansion of the CD4− iNKT cell subpopulation (i.e. presence or absence of expansion of the subpopulation in the analyzed biological sample), the recipient may require a treatment regime that is more or less aggressive than a standard regimen, or it may be determined that the recipient is best suited for a standard regimen. When so treated, one can treat or prevent complications associated with transplantation such as aGVHD. Conversely, the level of expansion of the CD4− iNKT cell subpopulation may indicate that the patient is not likely to experience an undesirable clinical outcome. In that event, the patient may avoid an immunosuppressive treatment (or require a less aggressive regimen) and their associated side effects.

Any immunosuppressive agent used in transplantation to control the rejection, or a combination of such agents, can be used according to the invention, such as prednisone, methyl prednisolone, azathioprine, cyclophosphamide, cyclosporine, monoclonal antibodies against T-cells, e.g. OKT3, and antisera to human lymphocytes (antilymphocyte globulin-ALS) or to *thymus* cells (antithymocyte globulin-ATG). Examples of myelo-ablative agents that can be used according to the invention are busulfan, dimethyl myleran and thiotepa.

Kits According to the Invention

The present invention is further directed to a kit suitable for carrying out the methods according to the invention. Such a kit may comprise at least a) an agent stimulating the proliferation of iNKT cells, b) an agent activating iNKT cells and c) a labelled agent specifically binding CD4 such as described above.

In one embodiment, the kit comprises at least IL-2, alpha-GalCer and a labelled antibody specifically binding CD4.

In a particular embodiment, the kit further comprises d) a labelled agent specifically binding CD3 (e.g. a labelled antibody specifically binding CD3) and e) a labelled agent specifically binding CD1d-restricted TCR Vα24Vβ11 of iNKT cells (e.g. pre-loaded human CD1d tetramer such as a CD1d/PBS-57 tetramer or those purchased from ProImmune).

The kit may further comprise one or more biochemical reagents useful for carrying out the method according to the invention (e.g. a buffer solution such as PBS and a wash buffer).

The invention will be further illustrated by the following figures and examples. However, these examples and figures should not be interpreted in any way as limiting the scope of the present invention.

FIGURES

FIG. 1: Representative FACS profile of (A) total iNKT cells stained with an anti-CD3 and a PBS57-loaded CD1d-tetramer (left) or an empty CD1d-tetramer used as a negative control (right), and (B) the CD4 expression profile of gated iNKT cells.

Figure 2:
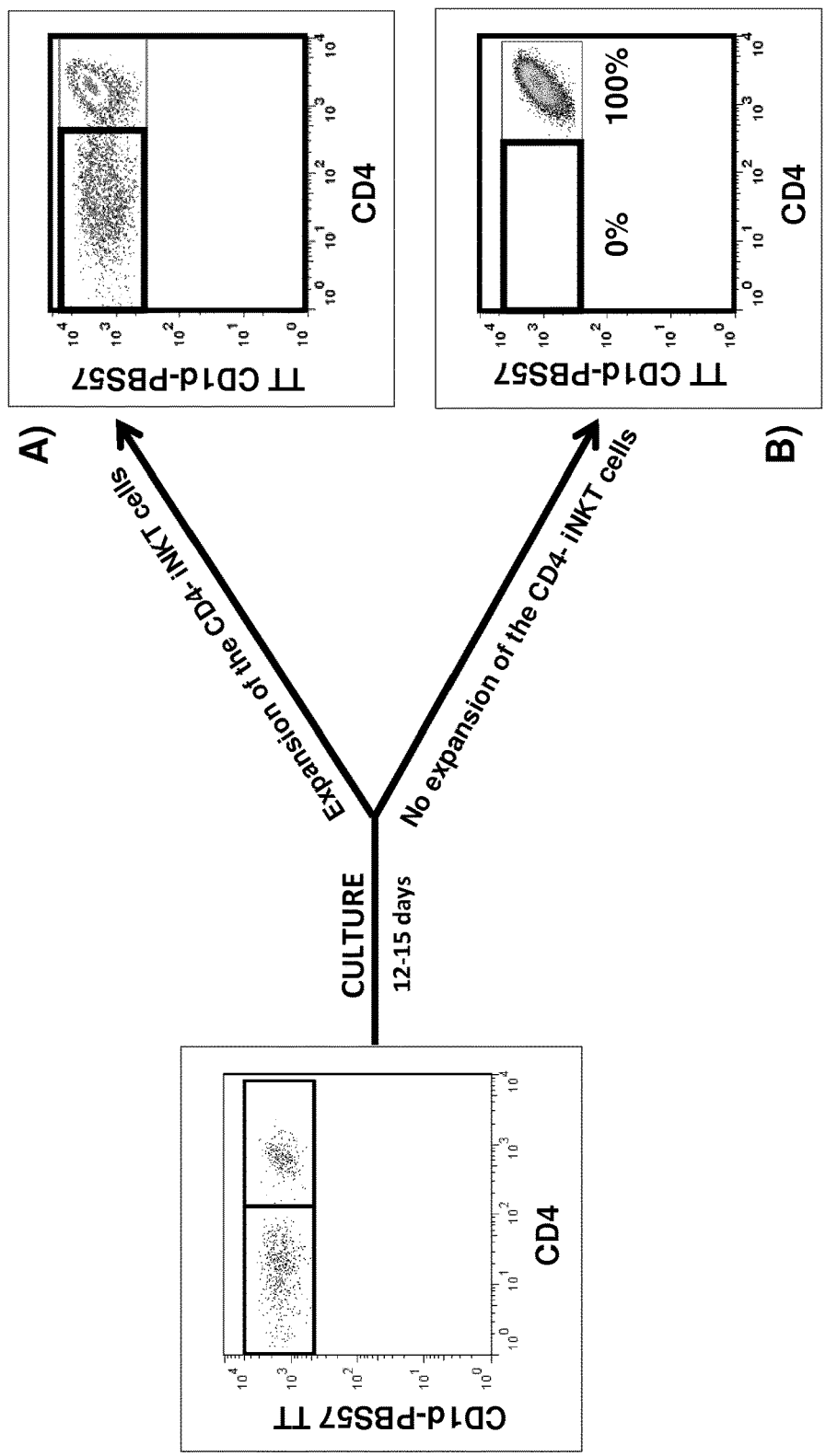

FIG. 2: Representation of the results of expansion of the CD4− iNKT cell population from donor grafts. (A) either the subpopulation CD4− iNKT is present and has expanded in culture from the population of iNKT or (B) the subpopulation CD4− iNKT is absent and/or has not expanded in culture from the population of iNKT.

Figure 3:
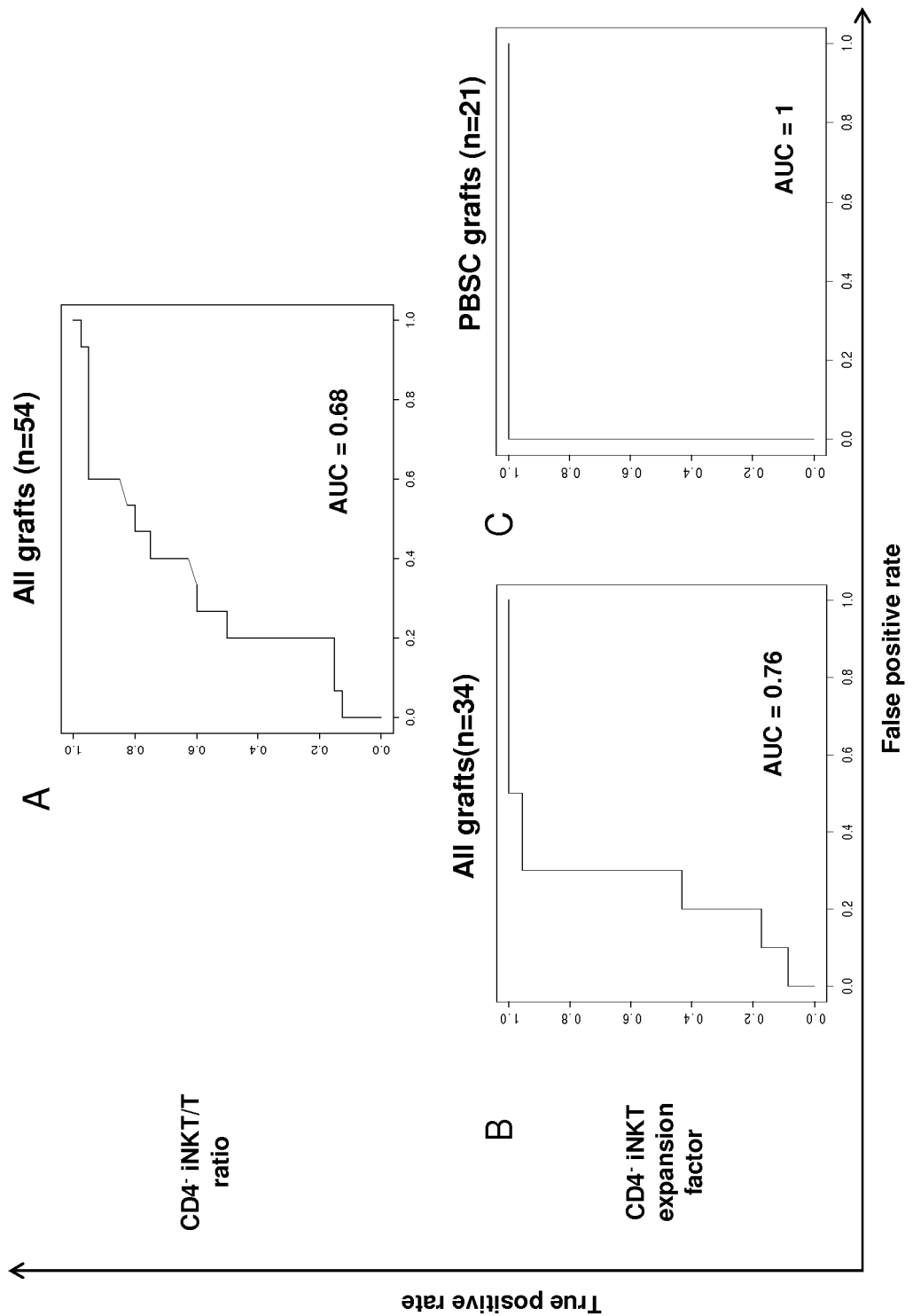

FIG. 3: ROC analyses predicting the risk of grade II-IV aGVHD. (A): predictive value of the graft CD4− iNKT/T ratio, (B) and (C): predictive value of the expansion factor of graft CD4− iNKT cells.

Figure 4:
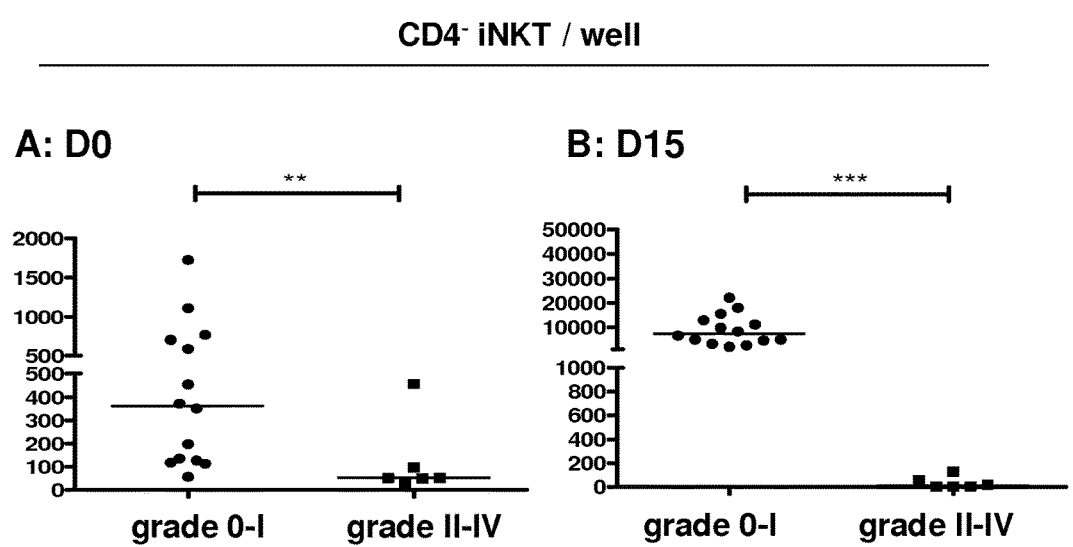

FIG. 4: Comparison of CD4− iNKT cells/well on day 0 (A) and on day 15 (B) of culture from PBSC grafts of patients developing grade 0-I versus grade II-IV aGVHD.

EXAMPLES

Analyses of the Graft Content and the Expansion Capacity of CD4− iNKT Cells from Either the Graft or the Peripheral Blood of HSCT Donors on the Occurrence of Acute GVHD in the Recipient after Transplantation Material & Methods iNKT cells expansion: Donors' PBMCs from blood or bone marrow samples are cultured in 24-well plates at a density of $10^6$ cells per well in RPMI 1640 medium containing 100 U/mL antibiotics (Penicillin+Streptomycin), 10% FBS, 2 mM glutamine, and 10 mM HEPES. 100 ng/mL alpha-galactosylceramide (KRN7000) is added at the onset of culture followed, 24 h later, by 50 ng/mL (or 845 UI/mL) of rhIL-2. After 2 weeks, cells are collected, extensively washed, and assayed for their viability by trypan blue exclusion.

Surface staining: Fresh or cultured donors' PBMCs are analyzed by flow cytometry. Staining of PBMCs is performed at 4° C. for 30 min in the presence of the following directly fluorescently-conjugated monoclonal antibodies: Human CD1d Tetramer Pre-loaded with alpha-GalCer (from ProImmune), anti-human CD3 and anti-human CD4 (from eBioscience). Cells are resuspended in PBS 1× plus 2% FBS and first stained with said Human CD1d Tetramer Pre-loaded with alpha-GalCer, washed with PSB 1×FBS 2%, and then stained with anti-CD3 and anti-CD4 antibodies. Cells are acquired on a FACSCanto II (BD Biosciences) and analyze using FlowJo software (Tree Star).

Patients and methods: The inventors have analyzed the content of HSC grafts in T cell subtypes including iNKT cells from 54 allogeneic donors (52% of matched related and 48% of matched unrelated) and could explore the expansion capacity of iNKT cells in 34 of them (14 bone marrow stem cells and 21 PBSC). The graft content proportions and absolute numbers of total, CD4− and CD4+ iNKT, CD4+, CD8+, γδ+ and naïve and memory activated regulatory T cells were analyzed by flow cytometry. The expansion capacity of the iNKT CD4+ and CD4− subpopulations was analysed after 15 days of PBMC culture with IL-2 and alpha-GalCer.

Results were correlated to the development of grade II to IV aGVHD in the recipients after allogeneic HSCT, which occurred in 15 of the 54 patients (28%), and from 6 of the 21 PBSC grafts (28.5%) that could be explored for the expansion capacity of iNKT subtypes.

Results

As shown in FIG. 1, the total iNKT cell population can be detected by flow cytometry in the CD3+ and CD1d-tetramer+ cells (FIG. 1A). The CD4− and CD4+ iNKT subpopulations are detected by the use of an anti-CD4 labelled antibody (FIG. 1B).

As shown in FIG. 2, after 12 to 15 days of in vitro expansion of iNKT cells in the presence of IL-2 and alpha-Gal-Cer, two distinct situations are observed depending of the expansion (2A) or not (2B) of the CD4− iNKT subpopulation.

In univariate analysis (Table 1), among the different explored lymphocyte subsets and functional analyses, only the total iNKT/T, CD4− iNKT/T ratios and the expansion capacity of CD4− iNKT cells were significantly associated with the occurrence of grade II-IV aGVHD (p=0.039, p=0.038 and p=0.008, respectively). Thus, as previously reported, in comparison to patients developing grade II-IV aGVHD, patients developing grade 0-I aGVHD had received a graft containing higher proportions of CD4− iNKT cells.

TABLE 1

Univariate analysis of the correlations between graft content in T cell subsets and the occurrence of grade II-IV aGVHD

| Variable | Grade II-IV aGVHD mean (SD) | | p-value |
|---|---|---|---|
| | yes | no | |
| CD34+ × $10^6$/kg | 4.2 (2.7) | 4 (2.1) | 0.9 |
| T CD3+ × $10^7$/kg | 29.9 (16.6) | 26.3 (14.6) | 0.44 |
| Total iNKT × $10^6$/kg | 0.16 (0.32) | 0.18 (0.23) | 0.29 |
| CD4+ iNKT × $10^6$/kg | 0.04 (0.08) | 0.07 (0.15) | 0.26 |
| CD4− iNKT × $10^6$/kg | 0.12 (0.27) | 0.14 (0.19) | 0.26 |
| LTCD4+ × $10^6$/kg | 86.1 (83.6) | 76.3 (88) | 0.5 |
| LTCD8+ × $10^6$/kg | 54.9 (55.1) | 56.3 (71.3) | 0.96 |
| LTCD3 γδ+ × $10^6$/kg | 12.8 (14.4) | 13.7 (19.3) | 0.5 |
| Total T regs × $10^6$/kg | 1.2 (1.7) | 1.5 (2.1) | 0.59 |
| Total iNKT/$10^3$T | 1.1 (1.3) | 1.9 (1.8) | 0.039 |
| CD4+ iNKT/$10^3$T | 0.3 (0.4) | 0.5 (0.7) | 0.13 |
| CD4− iNKT/$10^3$T | 0.7 (0.9) | 1.3 (1.5) | 0.038 |
| LTCD4+/$10^3$T | 580.6 (112.9) | 567 (109.6) | 0.68 |
| LTCD8+/$10^3$T | 375.5 (90.2) | 390.7 (88.2) | 0.57 |
| Total T regs/$10^3$T | 6.7 (4.5) | 9.9 (9.1) | 0.54 |
| LTCD3 γδ+/$10^3$T | 123.9 (82.3) | 129.4 (104.1) | 0.91 |
| Expansion factor.iNKT.CD4+ | 260.5 (317.9) | 287.8 (633.4) | 0.77 |
| Expansion factor.iNKT.CD4− | 15.7 (30.6) | 35.3 (43.0) | 0.008 |

In multivariate analysis (Table 2), the expansion capacity of the CD4− iNKT cells contained in the graft was an independent predictive factor of the occurrence of grade II-IV aGVHD (Odds Ratio=0.19, 95% CI: 0.029-0.55, p=0.017) as well as the use of an unrelated donor (p=0.028).

TABLE 2

Multivariate analysis of the impact of transplant characteristics on the occurrence of grade II-IV aGVHD

| | OR | [95% CI] | p-value |
|---|---|---|---|
| Expansion factor of CD4− iNKT cells | 0.19 | [0.029-0.55] | 0.017 |
| Recipient age | 0.88 | [0.67-1.01] | 0.18 |
| Donnor age | 1.13 | [0.99-1.4] | 0.14 |
| MRD versus MUD | $6.6 \cdot 10^{-4}$ | [$1.1 \cdot 10^{-8}$-$7.6 \cdot 10^{-2}$] | 0.028 |

Using ROC analyses (FIG. 3), the inventors found that the expansion factor of the CD4− iNKT cells contained in the graft was the best predictive factor of the occurrence of grade II-IV aGVHD (Area Under the Curve (AUC)=0.76). All grafts included, the sensitivity of the test was 96% (probability of developing aGVHD with an expansion factor below 1.8) and the specificity of 70% (probability of not developing aGVHD above the cut-off). In PBSC grafts (n=21 with 6 grade II-IV aGVHD) the predictivity of the test was even better with an AUC=1 and a sensitivity and specificity of 100% (FIGS. 3 and 4).

In 15 donors, the inventors observed similar patterns of expansion capacity of CD4− iNKT cells from either the peripheral blood before mobilization by G-CSF or the graft (Table 3).

TABLE 3

Comparison of the expansion capacity of CD4− iNKT cells from graft or peripheral blood samples in 12 PBSC and 3 BMC analyzed donors

| Donor No | Type of graft | Expansion capacity of CD4− iNKT cells from | |
|---|---|---|---|
| | | HSC graft | Peripheral blood |
| 1 | PBSC | + | + |
| 2 | PBSC | + | + |
| 3 | PBSC | + | + |
| 4 | PBSC | − | − |
| 5 | PBSC | + | + |
| 6 | PBSC | + | + |
| 7 | PBSC | + | + |
| 8 | PBSC | + | + |
| 9 | PBSC | + | + |
| 10 | PBSC | + | + |
| 11 | PBSC | + | + |
| 12 | PBSC | + | + |
| 13 | BMC | + | + |
| 14 | BMC | + | + |
| 15 | BMC | + | + |

REFERENCES

Throughout this application, various references describe the state of the art to which this invention pertains. The disclosures of these references are hereby incorporated by reference into the present disclosure.

Chaidos A, Patterson S, Szydlo R, Chaudhry M S, Dazzi F, Kanfer E, McDonald D, Marin D, Milojkovic D, Pavlu J, Davis J, Rahemtulla A, Rezvani K, Goldman J, Roberts I, Apperley J, Karadimitris A; Graft invariant natural killer T-cell dose predicts risk of acute graft-versus-host disease in allogeneic hematopoietic stem cell transplantation; Blood. 2012 May 24; 119(21):5030-6.

Rubio M T, Moreira-Teixeira L, Bachy E, Bouillié M, Milpied P, Coman T, Suarez F, Marcais A, Sibon D, Buzyn A, Caillat-Zucman S, Cavazzana-Calvo M, Varet B, Dy M, Hermine O, Leite-de-Moraes M. Early posttransplantation donor-derived invariant natural killer T-cell recovery predicts the occurrence of acute graft-versus-host disease and overall survival. Blood. 2012 Sep. 6; 120(10):2144-54.

The invention claimed is:

1. A method for determining whether the population of invariant NKT (iNKT) cells from a biological sample of a candidate human transplant donor expands, comprising the following steps:
    i) measuring the CD4− iNKT cell subpopulation in the population of invariant NKT (iNKT) cells of a biological sample obtained from the candidate human transplant donor, wherein said candidate human transplant donor is a human leukocyte antigen (HLA)-identical donor, an HLA-matched donor, an HLA haploidentical donor, and/or a 4/6 to 6/6 HLA (A, B, DR) cord blood donor;

ii) expanding the population of iNKT cells from the biological sample obtained from the candidate human transplant donor; and iii) detecting the presence or absence of expansion of the CD4− iNKT cell subpopulation in the population obtained at step ii).

2. The method according to claim 1, wherein the step ii) of expanding the population of iNKT cells is carried out by (a) isolating peripheral blood mononuclear cells (PBMCs) from the biological sample obtained from said candidate human transplant donor, and (b) culturing said PBMCs in a medium comprising both an agent stimulating the proliferation of iNKT cells and an agent activating iNKT cells.

3. The method according to claim 1 or claim 2, wherein the CD4− iNKT cell subpopulation is a population of CD3+CD4− TCR Vα24Vβ11 cells.

4. The method according to claim 2, wherein the agent stimulating the proliferation of iNKT cells is interleukin 2 (IL-2).

5. The method according to claim 2, wherein the agent activating iNKT cells is a glycolipid antigen selected from the group consisting of alpha-galactosylceramide (alpha-GalCer), alpha-glucuronosylceramide, phosphatidylinositoltetramannoside, isoglobotrihexosylceramide, ganglioside GD3, phosphatidylcholine, phosphatidylethanolamine, phosphatidylinositol, sulfatide, beta-galactosylceramide, lipophosphoglycan, glycoinositol phospholipid, beta-anomeric galactoceramide and alpha-anomeric galactosylceramide, and bacterial lipid antigens.

6. The method according to claim 5, wherein the glycolipid antigen is alpha-GalCer.

7. The method according to claim 3 wherein the agent stimulating the proliferation of iNKT cells is interleukin 2 (IL-2).

8. The method according to claim 3 wherein the agent activating iNKT cells is a glycolipid antigen selected from the group consisting of alpha-galactosylceramide (alpha-GalCer), alpha-glucuronosylceramide, phosphatidylinositoltetramannoside, isoglobotrihexosylceramide, ganglioside GD3, phosphatidylcholine, phosphatidylethanolamine, phosphatidylinositol, sulfatide, beta-galactosylceramide, lipophosphoglycan, glycoinositol phospholipid, beta-anomeric galactoceramide and alpha-anomeric galactosylceramide, and bacterial lipid antigens.

9. The method according to claim 8, wherein the glycolipid antigen is alpha-GalCer.

10. The method according to claim 4 wherein the agent activating iNKT cells is a glycolipid antigen selected from the group consisting of alpha-galactosylceramide (alpha-GalCer), alpha-glucuronosylceramide, phosphatidylinositoltetramannoside, isoglobotrihexosylceramide, ganglioside GD3, phosphatidylcholine, phosphatidylethanolamine, phosphatidylinositol, sulfatide, beta-galactosylceramide, lipophosphoglycan, glycoinositol phospholipid, beta-anomeric galactoceramide and alpha-anomeric galactosylceramide, and bacterial lipid antigens.

11. The method according to claim 10, wherein the glycolipid antigen is alpha-GalCer.

12. A method of transplanting a tissue or organ comprising:
i) measuring the CD4− iNKT cell subpopulation in the population of invariant NKT (iNKT) cells of a biological sample obtained from a candidate human tissue or organ transplant donor, wherein said candidate human transplant donor is a human leukocyte antigen (HLA)-identical donor, an HLA-matched donor, an HLA haploidentical donor, and/or a 4/6 to 6/6 HLA (A, B, DR) cord blood donor;
ii) expanding the population of iNKT cells from the biological sample obtained from the candidate human transplant donor;
iii) detecting the presence or absence of expansion of the CD4− iNKT cell subpopulation in the population obtained at step ii); and
iv) transplanting a tissue or organ from the candidate donor into a transplant recipient if expansion of the CD4− iNKT cell subpopulation is detected in step iii).

* * * * *